(12) United States Patent
Stern

(10) Patent No.: US 6,440,392 B1
(45) Date of Patent: Aug. 27, 2002

(54) NASAL CALCITONIN FORMULATIONS

(75) Inventor: William Stern, Tenafly, NJ (US)

(73) Assignee: Unigene Laboratories, Inc., Fairfield, NJ (US)

( * ) Notice: Subject to any disclaimer, the term of this patent is extended or adjusted under 35 U.S.C. 154(b) by 0 days.

(21) Appl. No.: 09/776,537

(22) Filed: Feb. 2, 2001

Related U.S. Application Data

(60) Provisional application No. 60/180,241, filed on Feb. 4, 2000.

(51) Int. Cl.$^7$ .............................. A61K 9/12; A61K 9/00; A61K 38/23
(52) U.S. Cl. ........................... 424/43; 424/45; 424/455; 514/2; 514/3; 514/12
(58) Field of Search ............................ 424/43, 45, 455; 514/2, 3, 12

(56) References Cited

U.S. PATENT DOCUMENTS

| | | | |
|---|---|---|---|
| 5,059,587 A | 10/1991 | Yamamoto et al. ............ | 514/12 |
| 5,665,700 A | * 9/1997 | Cho et al. ....................... | 514/2 |
| 6,087,338 A | 7/2000 | Veronesi et al. ............... | 514/21 |
| 6,149,893 A | * 11/2000 | Mardente et al. .............. | 424/45 |

OTHER PUBLICATIONS

Dua et al, International Journal of Pharmaceutics 147, 1997—pp. 233–242 "The influence of tonicity and viscosity on the intranasal absorption of salmon calcitonin in rabbits".*

* cited by examiner

Primary Examiner—Jose' G. Dees
Assistant Examiner—Mina Haghighatian
(74) Attorney, Agent, or Firm—Ostrolenk, Faber, Gerb & Soffen, LLP

(57) ABSTRACT

A liquid pharmaceutical composition is disclosed comprising calcitonin or an acid addition salt thereof and citric acid or salt thereof in a concentration from about to about 50 mM, said composition being in a form table for nasal administration.

23 Claims, No Drawings

NASAL CALCITONIN FORMULATIONS

RELATED APPLICATIONS

This application is based upon and claims priority of U.S. Provisional Application No. 60/180,241, filed Feb. 4, 2000, which is hereby incorporated by reference.

BACKGROUND OF THE INVENTION

1. Field of the Invention

The present invention relates to an intranasal pharmaceutical compositions comprising calcitonin as an active ingredient and specific concentrations of citric acid or a salt thereof as a stabilizer and absorption enhancer.

2. Description of the Related Art

Calcitonins are a class of polypeptide hormones that are used in the treatment of a variety of conditions including osteoporosis, Paget's disease and malignant hypercalcemia. They are composed of amino acids and have been extracted from a number of sources including salmon, porcine, eel and human. Calcitonins with amino acid sequences identical to the natural forms have been produced by chemical synthesis as well as by recombinant technology.

Given their size and chemical composition, calcitonins were originally administered by subcutaneous or intramuscular injection. Other routes of administration were technically difficult because calcitonins were poorly absorbed through tissue and were readily degraded by bodily fluids. Despite these obstacles, a formulation (U.S. Pat. No. 5,759,565) was developed that could be administered via the nasal route. The nasal formulation was designed to be stored in a multi-dose container that was stable for an extended period of time and resisted bacterial contamination. The preservative in the formulation, benzalkonium chloride, was found to enhance the absorption of salmon calcitonin. However, benzalkonium chloride was reported (P. Graf et al., Clin. Exp. Allergy 25:395–400; 1995) to aggravate rhintis medicamentosa in healthy volunteers who were given a decongestant nasal spray containing the preservative. It also had an adverse effect on nasal mucosa (H. Hallen et al., Clin. Exp. Allergy 25:401–405; 1995). Berg et al. (Laryngoscope 104:1153–1158; 1994) disclose that respiratory mucosal tissue that was exposed in vitro underwent severe morphological alterations. Benzalkonium chloride also caused significant slowing of the mucocilary transport velocity in the ex vivo frog palate test (P.C. Braga et al., J. Pharm. Pharmacol. 44:938–940; 1992).

SUMMARY OF THE INVENTION

Accordingly, the present invention provides a liquid pharmaceutical composition comprising calcitonin or an acid addition salt thereof and citric acid and/or salt thereof in a concentration from about 10 to about 50 mM, said composition being in a form suitable for nasal administration.

The present invention also provides a liquid pharmaceutical composition comprising about 2,200 MRC units of salmon calcitonin, about 10 mM citric acid, about 0.2% phenylethyl alcohol, about 0.5% benzyl alcohol, and about 0.1% TWEEN® 80.

The present invention further provides a liquid pharmaceutical composition comprising about 2,200 MRC units of salmon calcitonin, about 20 mM citric acid, about 0.2% phenylethyl alcohol, about 0.5% benzyl alcohol, and about 0.1% TWEEN® 80.

The present invention also provides a method of administering a calcitonin to a subject requiring calcitonin treatment, which method comprises administering via the nasal route to said subject a liquid pharmaceutical composition comprising calcitonin or an acid addition salt thereof and citric acid or salt thereof in a concentration from about 10 to about 50 mM.

The present invention further provides a method of improving the stability of a liquid pharmaceutical composition of calcitonin comprising adding citric acid or a salt thereof in a concentration from about 10 to about 50 mM to said composition.

The present invention also provides a method of improving the bioavailability or the concentration of plasma calcitonin in a subject following nasal administration of a liquid pharmaceutical composition of calcitonin, which method comprises adding citric acid or a salt thereof in a concentration from about 10 to about 50 mM to said composition prior to said administration.

DETAILED DESCRIPTION OF THE INVENTION

In accordance with the present invention it has now been surprisingly found that pharmaceutical compositions can be obtained comprising a calcitonin as active ingredient which meet the high standards of stability and bioavailability required for nasal application and which are, for example, eminently suitable for use in multiple dose nasal spray applicators, i.e., applicators capable of delivering a series of individual dosages over, e.g., period of several days or weeks, by the use of citric acid or a salt thereof in concentrations ranging from about 10 to about 50 mM as a buffering agent.

Surprisingly, it has also been found that use of citric acid or a salt thereof at increasing concentrations confers beneficial advantages in relation to the nasal absorption characteristics of calcitonin containing compositions and hence enhance calcitonin bioavailability levels consequential to nasal application. In addition, it has also been found that the use of citric acid or a salt thereof in concentrations ranging from about 10 to about 50 mM increase the stability of calcitonin containing compositions while at the same time higher concentrations of citric acid or salt thereof did not have the same stabilizing effect.

The calcitonins for use in the invention may be in free form or in pharmaceutically acceptable salt or complex form, e.g. in pharmaceutically acceptable acid addition salt form. Such salts and complexes are known and possess an equivalent degree of activity and tolerability to the free forms. Suitable acid addition salt forms for use in accordance with the invention include for example the hydrochlorides and acetates.

The above defined compositions may be applied in accordance with the invention to the nasal mucosa, e.g. either in drop or in spray form. As hereinafter described however, they are most preferably applied in spray form, i.e., in the form of finely divided droplets.

The compositions of the invention may of course also include additional ingredients, in particular components belonging to the class of conventional pharmaceutically applicable surfactants. In this connection it has in accordance with a further aspect of the present invention been found that the use of surface active agents generally in relation to the nasal application of calcitonins, in particular salmon calcitonin, may increase absorption via the nasal mucosa and hence improve obtained bioavailability rates.

Preferably, the liquid pharmaceutical calcitonin composition of the present invention contains a pharmaceutically acceptable, a liquid diluent or carrier suitable for application to the nasal mucosa, most preferably aqueous saline.

The compositions of the invention are formulated so as to permit administration via the nasal route. For this purpose they may also contain, e.g. minimum amounts of any additional ingredients or excipients desired, for example, additional preservatives or, e.g. ciliary stimulants such as caffeine.

Generally for nasal administration a mildly acid pH will be preferred. Preferably the compositions of the invention have a pH of from about 3 to 5, more preferably from about 3.5 to about 3.9 and most preferably 3.7. Adjustment of the pH is achieved by addition of an appropriate acid, such as hydrochloric acid.

The compositions of the invention should also possess an appropriate isotonicity and viscosity. Preferably they have an osmotic pressure of from about 260 to about 380 mOsm/liter. Desired viscosity for the nasal spray is preferably less than 0.98 cP.

Compositions in accordance with the present invention may also comprise a conventional surfactant, preferably a non-ionic surfactant.

When a surfactant is employed, the amount present in the compositions of the invention will vary depending on the particular surfactant chosen, the particular mode of administration (e.g. drop or spray) and the effect desired. In general, however, the amount present will be of the order of from about 0.1 mg/ml to about 10 mg/ml, preferably about 0.5 mg/ml to 5 mg/ml and most preferably about 1 mg/ml.

The amount of calcitonin to be administered in accordance with the method of the invention and hence the amount of active ingredient in the composition of the invention will, of course, depend on the particular calcitonin chosen, the condition to be treated, the desired frequency of administration and the effect desired.

As indicated in the following examples, bioavailability for calcitonins, in particular salmon calcitonin, as determined in terms of blood-plasma concentration following nasal administration in accordance with the teachings of the present invention has been found to be surprisingly high.

For nasal administration in accordance with the present invention, treatment will therefore suitably comprise administration of dosages of from about 50 to about 400 MRC units, more preferably from about 100 to about 200 MRC units at a frequency of from about once daily to about three times weekly. Conveniently dosages as aforesaid will be administered in a single application, i.e., treatment will comprise administration of single nasal dosages comprising about 50 to about 400 MRC units, preferably about 100 to about 200 MRC units, calcitonin. Alternatively such dosages may be split over a series of 2 to 4 applications taken at intervals during the day, the dosage at each application then comprising about 10 to about 200, preferably about 25 to about 100 MRC units.

The total composition quantity administered at each nasal application suitably comprises from about 0.05 to 0.15 ml, typically about 0.1 ml. Compositions for use in accordance with the invention accordingly suitably comprise from about 150 to about 8,000, preferably from about 500 to about 4,000, more preferably from about 500 to about 3,000, yet again more preferably from about 1,000 to about 2,500, and most preferably about 2,200 MRC units of calcitonin per ml.

For the purposes of nasal administration, the compositions of the invention will preferably be put up in a container provided with means enabling application of the contained composition to the nasal mucosa, e.g. put up in a nasal applicator device. Suitable applicators are known in the art and include those adapted for administration of liquid compositions to the nasal mucosa in drop or spray form. Since dosaging with calcitonins should be as accurately controlled as possible use of spray applicators for which the administered quantity is susceptible to precise regulation will generally be preferred. Suitable administrators include, e.g. atomizing devices, e.g. pump-atomizers and aerosol dispensers. In the latter case, the applicator will contain a composition in accordance with the invention together with a propellant medium suitable for use in a nasal applicator. The atomizing device will be provided with an appropriate spray adaptor allowing delivery of the contained composition to the nasal mucosa. Such devices are well known in the art.

The container, e.g. nasal applicator, may contain sufficient composition for a single nasal dosaging or for the supply of several sequential dosages, e.g. over a period of days or weeks. Quantities of individual dosages supplied will preferably be as hereinbefore defined. The stability of the compositions of the invention may be determined in conventional manner. As indicated hereinbelow, the calcitonin content of the compositions of the invention will degrade less than 50 % in 15 days at 50° C. as indicated by standard analytical tests.

EXPERIMENTAL DESIGN—METHODS OF ADMINISTERING NASAL CALCITONIN AND MEASUREMENT OF PLASMA CONCENTRATION

Female Wistar rats, weighing between 225 and 250 g are anesthetized with a combination of ketamine and xyalzine, and a cannula is inserted into the carotid artery. The cannula is fitted to a three-way valve through which blood is sampled and replaced with physiological saline containing heparin. Formulated salmon calcitonin (sCT) (5 $\mu$g per 25 $\mu$l) is administered intranasally through a micropipette tip that was inserted 8 mm into the rat's nostril. For single-dose studies, 5 $\mu$g of sCT was administered. In multiple dose studies, sCT was administered four times in a volume of 25 $\mu$l each at 0, 30, 60 and 90 minutes for a total dose of 20 $\mu$g.

In single-dose studies, blood samples are collected prior to dosing and at 5, 15, 30, 60 and 120 minutes after dosing. In multiple-dose studies, blood samples are collected prior to dosing and at 30, 60, 90, 120 and 150 minutes after the administration of the first dose. Blood samples are always collected immediately before the administration of any additional costs.

Each sample (0.5 ml) of blood is collected into a heparinized 1 ml syringes and then transferred to chilled 1.5 ml polypropylene tubes containing 10 $\mu$l of heparin (500 U per ml). The tubes are centrifuged at approximately 3000 rpm for 20 minutes at 2–8° C. and the plasma supernatant is transferred to microcentrifuge tubes that were stored at −20° C. The concentration of sCT in plasma is determined by a competitive radioimmunoassay. Aliquots of the plasma samples and standards are incubated for 4 hours at room temperature with rabbit anti-sCT antibody. Subsequently, $^{125}$I-sCT is added and incubated overnight at 2–8° C. Antibody-bound $^{125}$I-sCT is isolated the next day by precipitating it with normal rabbit antiserum and goat anti-rabbit antibody. Radioactivity associated with the resulting pellets is measured with a gamma counter. The concentration of sCT in plasma is inversely proportional to the amount of radioactivity that was precipitated.

The values of Cmax are determined by inspection and the values for bioavailability (relative to an intravenous injection) are calculated from the areas under the curve that were obtained from plots of plasma sCT concentration as a function of time.

EXAMPLE 1

The following study examines the effect of the concentration of citric acid on the bioavailability and plasma concentration of nasally administered salmon calcitonin. Rats were administered intranasally as described previously 20 µl of rsCT (200 µg/ml) in 0.85% sodium chloride, 0.1% TWEEN® 80, 0.2% phenylethyl alcohol, 0.5% benzyl alcohol and varying amounts of citric acid adjusted to pH 3.7 at t=0, 20, 60 and 90 minutes. Samples of blood were taken prior to the administration of rsCT at these time points as well as at t=120 and 150 minutes. The resulting plasma samples were analyzed for rsCT by radioimmunoassay. Maximum rsCT levels were detected at t=120 minutes. The results of this study as shown in Table 1 indicate that the bioavailability and peak concentration of rsCT was a function of the concentration of citric acid in the formulation.

TABLE 1

EFFECT OF THE CONCENTRATION OF CITRIC ACID
ON THE BIOAVAILABILITY AND PLASMA
CONCENTRATION OF SALMON CALCITONIN
ADMINISTERED INTRANASALLY TO RATS

| Citric acid (pH 3.7) | Bioavailability (percent ± sdev) | Maximum plasma sCT (ng/ml ± sdev) |
|---|---|---|
| 0 | 0.89 ± 0.19 | 1.10 ± 0.52 |
| 10 | 3.14 ± 1.77 | 3.66 ± 1.67 |
| 25 | 5.01 ± 2.34 | 5.11 ± 2.09 |
| 50 | 6.15 ± 1.31 | 6.05 ± 1.30 |
| 100 | 13.36 ± 3.38 | 12.98 ± 3.96 |

EXAMPLE 2

The following study examines the effect of different preservatives on the plasma concentration of nasally administered salmon calcitonin. Rats were administered intranasally as described previously 20 µl of sCT (200 µg/ml) in 0.85% sodium chloride, 0.1% TWEEN® 80 and a combination preservatives of either 0.2% phenylethyl alcohol and 0.5% benzyl alcohol or 0.27% methyl parabens and 0.04% propyl parabens at t=0, 30, 60 and 90 minutes. The results of this study as shown in Table 2 indicate that the bioavailability and peak concentration of rsCT are not significantly affected by the addition of the different preservatives.

TABLE 2

EFFECT OF PRESERVATIVES ON THE
AVAILABILITY AND PLASMA CONCENTRATION
OF SCT ADMINISTERED INTRANASALLY TO RATS

| Preservatives | Bioavailability (percent ± sdev) | Maximum plasma sCT (ng/ml ± sdev) |
|---|---|---|
| None | 1.14 ± 0.87 | 1.24 ± 0.79 |
| 0.2% phenylethyl alcohol - 0.5% benzyl alcohol | 0.89 ± 0.19 | 1.10 ± 0.52 |
| 0.27 methyl parabens - 0.04% propyl parabens | 1.08 ± 0.86 | 1.47 ± 1.46 |

EXAMPLE 3

The following study examines the effect of the concentration of citric acid on the stability of salmon calcitonin stored for varying periods at a temperature of 50° C. Nasal formulations containing sCT (200 µg/ml), 0.25% phenylethyl alcohol, 0.5% benzyl alcohol and 0.1% TWEEN® 80 were adjusted to pH 3.7 with either HCl or the indicated amount of buffered citric acid. The formulations were stored at 50° C. in sealed glass containers for the indicated amount of time and analyzed for sCT by high performance liquid chromatography. The results as shown in Table 3 indicate that in the absence of citric acid, the amount sCT in the formulation decreased steadily between 0 and 9 days after the study was begun. In the presence of citric acid (10–50 mM) the rate of disappearance of sCT decreased significantly. However, as the concentration of citric acid was further increased, the rate of sCT disappearance from vials stored at 50° C. increased in proportion to the amount of buffered citric acid in the formulation.

TABLE 3

EFFECT OF THE CONCENTRATION OF
CITRIC ACID ON THE STABILITY OF
sCT STORED FOR VARYING PERIODS AT 50° C.
Percent sCT Recovered

| Citric Acid (pH 3.7) | 0 mM | 10 mM | 20 mM | 50 mM | 100 mM |
|---|---|---|---|---|---|
| Days at 50° C. | | | | | |
| 0 | 100 | 100 | 100 | 100 | 100 |
| 3 | 83 | 94 | 91 | 90 | 87 |
| 6 | 53 | 90 | 87 | 83 | 77 |
| 9 | 24 | 82 | 78 | 73 | 66 |
| 15 | 22 | 74 | 68 | 61 | 20 |

What is claimed is:

1. A liquid pharmaceutical composition comprising calcitonin or an acid addition salt thereof and citric acid and/or salt thereof in a concentration from 10 to about 50 mM, said composition being in a form suitable for nasal administration.

2. The liquid pharmaceutical composition of claim 1 further comprising a pharmaceutically acceptable, aqueous liquid nasal carrier.

3. The liquid pharmaceutical composition of claim 2, wherein said carrier comprises aqueous saline.

4. The liquid pharmaceutical composition of claim 1, wherein said composition is in the form of a nasal spray.

5. The liquid pharmaceutical composition of claim 4 having a viscosity of less than 0.98 cP.

6. The liquid pharmaceutical composition of claim 1, wherein the calcitonin is selected from the group consisting of salmon calcitonin, human calcitonin, porcine calcitonin and 1,7-Asu-eel calcitonin.

7. The liquid pharmaceutical composition of claim 1, wherein the calcitonin is salmon calcitonin.

8. The liquid pharmaceutical composition of claim 1, wherein said calcitonin, or salt is present in an amount of from about 100 to about 8,000 MRC units/ml.

9. The liquid pharmaceutical composition of claim 1, wherein said calcitonin, or salt is present in an amount of from about 500 to about 4,000 MRC units/ml.

10. The liquid pharmaceutical composition of claim 1, wherein said calcitonin, or salt is present in an amount of from about 500 to about 3,000 MRC units/ml.

11. The liquid pharmaceutical composition of claim 1, wherein said calcitonin, or salt is present in an amount of from about 1,000 to about 2,500 MRC units/ml.

12. The liquid pharmaceutical composition of claim 1 having a pH of from about 3 to about 5.

13. The liquid pharmaceutical composition of claim 1 having a pH of from about 3.5 to about 3.9.

14. The liquid pharmaceutical composition of claim 1 having a pH of about 3.7.

15. The liquid pharmaceutical composition of claim 1 having an osmotic pressure of from about 250 to about 350 mOsm/liter.

16. The liquid pharmaceutical composition of claim 1 further containing at least 0.1% by weight of polyoxyethylene(20) sorbitan monooleate.

17. The liquid pharmaceutical composition of claim 1 further containing at least one preservative selected from the group consisting of benzyl alcohol, phenylethyl alcohol, methyl parabens, ethyl parabens, propyl parabens and butyl parabens.

18. A liquid pharmaceutical composition comprising about 2,200 MRC units of salmon calcitonin, about 10 mM citric acid, about 0.2% phenylethyl alcohol, about 0.5% benzyl alcohol, and about 0.1% polyoxyethylene(20) sorbitan monooleate.

19. A liquid pharmaceutical composition comprising about 2,200 MIC units of salmon calcitonin, about 20 mM citric acid, about 0.2% phenylethyl alcohol, about 0.5% benzyl alcohol, and about 0.1% polyoxyethylene(20) sorbitan monooleate.

20. A method of administering a calcitonin to a subject requiring calcitonin treatment, which method comprises administering to said subject a composition as defined in claim 1 via the nasal route.

21. The method of claim 20, wherein the amount of calcitonin administered is from about 200 to about 600 MRC units.

22. A method of improving the stability of a liquid pharmaceutical composition of calcitonin comprising adding citric acid or a salt thereof in a concentration from 10 to about 50 mM to said composition.

23. A method of improving the bioavailability or the concentration of plasma calcitonin in a subject following nasal administration of a liquid pharmaceutical composition of calcitonin, which method comprises adding citric acid or a salt thereof in a concentration from 10 to about 50 mM to said composition prior to said administration.

* * * * *